US011266736B2

(12) United States Patent
Dangerfield et al.

(10) Patent No.: US 11,266,736 B2
(45) Date of Patent: *Mar. 8, 2022

(54) METHOD OF PAINTING MICRO VESICLES

(71) Applicant: VIN DE BONA TRADING COMPANY PTE LTD, Singapore (SG)

(72) Inventors: John Dangerfield, Singapore (SG); Eva Maria Brandtner, Bregenz (AT); Wee Jin Tan, Singapore (SG); Christoph Metzner, Niederhollabrunn (AT)

(73) Assignee: VIN DE BONA TRADING COMPANY PTE LTD, Singapore (SG)

( * ) Notice: Subject to any disclaimer, the term of this patent is extended or adjusted under 35 U.S.C. 154(b) by 708 days.

This patent is subject to a terminal disclaimer.

(21) Appl. No.: 15/909,194

(22) Filed: Mar. 1, 2018

(65) Prior Publication Data

US 2018/0185472 A1 Jul. 5, 2018

Related U.S. Application Data

(63) Continuation-in-part of application No. 14/860,107, filed on Sep. 21, 2015, now Pat. No. 9,919,046, and a continuation-in-part of application No. 14/432,998, filed as application No. PCT/EP2013/071366 on Oct. 11, 2013, now abandoned, said application No. 14/860,107 is a continuation of application No. 12/988,046, filed as application No. PCT/EP2009/054016 on Apr. 3, 2009, now Pat. No. 9,139,817.

(60) Provisional application No. 61/712,471, filed on Oct. 11, 2012.

(30) Foreign Application Priority Data

Apr. 17, 2008 (EP) .................................... 08154748

(51) Int. Cl.
| | | |
|---|---|---|
| A61K 9/127 | (2006.01) |
| A61K 39/12 | (2006.01) |
| C12N 7/00 | (2006.01) |
| A61K 39/265 | (2006.01) |
| C12Q 1/04 | (2006.01) |
| B01D 15/38 | (2006.01) |
| A61K 39/00 | (2006.01) |

(52) U.S. Cl.
CPC .......... *A61K 39/265* (2013.01); *A61K 9/1271* (2013.01); *A61K 39/12* (2013.01); *B01D 15/3804* (2013.01); *C12N 7/00* (2013.01); *C12Q 1/04* (2013.01); *A61K 2039/525* (2013.01); *A61K 2039/5258* (2013.01); *A61K 2039/55555* (2013.01); *C12N 2710/16734* (2013.01); *C12N 2710/16751* (2013.01); *C12N 2740/10043* (2013.01); *C12N 2740/15043* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,783,401 A | 11/1988 | Horan et al. |
| 5,582,981 A | 12/1996 | Toole et al. |
| 5,840,867 A | 11/1998 | Toole et al. |
| 6,235,483 B1 | 5/2001 | Wolber et al. |
| 6,525,154 B1 | 2/2003 | Shea et al. |
| 6,812,023 B1 | 11/2004 | Lamparski et al. |
| 6,899,863 B1 | 5/2005 | Dhellin et al. |
| 7,198,923 B1 | 4/2007 | Abrignani et al. |
| 7,332,553 B2 | 2/2008 | Sellergren et al. |
| 7,384,589 B2 | 6/2008 | Hart et al. |
| 9,139,817 B2 | 9/2015 | Dangerfield et al. |
| 9,919,046 B2 | 3/2018 | Dangerfield et al. |
| 2008/0038281 A1 | 2/2008 | Altin et al. |
| 2011/0177156 A1 | 7/2011 | Szoka, Jr. et al. |
| 2015/0233800 A1 | 8/2015 | Dangerfield et al. |
| 2016/0206730 A1 | 7/2016 | Dangerfield et al. |

FOREIGN PATENT DOCUMENTS

| | | |
|---|---|---|
| WO | 9309221 A1 | 5/1993 |
| WO | 0017374 A1 | 3/2000 |
| WO | 03050290 A2 | 6/2003 |
| WO | 2005118802 A2 | 12/2005 |
| WO | 2009019215 A1 | 2/2009 |

(Continued)

OTHER PUBLICATIONS

Accession No. P13987, CD59_HUMAN in UniProtKB/Swiss-Prot, integrated in Jan. 1, 1990. Accessed online Jan. 27, 2011 at http://www.uniprot.org/uniprot/P13987#section_general—10 pages.
Aloia et al., Lipid composition and fluidity of the human immunodeficiency virus envelope and host cell plasma membranes. Proc Natl Acad Sci U S A. Jun. 1, 1993;90(11):5181-5185.
Beer et al., Amphotropic murine leukaemia virus envelope protein is associated with cholesterol-rich microdomains. Virol J. Apr. 19, 2005;2:36 (9 pages).
Booth et al., Exosomes and HIV Gag bud from endosome-like domains of the T cell plasma membrane. J Cell Biol. Mar. 13, 2006;172(6):923-935 (incl Supplementary data—1 additional page).
Breun et al., Protection of MLV Vector Particles from Human Complement. Biochem Biophys Res Commun. Oct. 14, 1999;264(1):1-5.

(Continued)

*Primary Examiner* — Stacy B Chen
(74) *Attorney, Agent, or Firm* — Acuity Law Group, PC; Michael A. Whittaker

(57) ABSTRACT

The present invention relates to a method to modify and/or to isolate exosomes and other naturally occurring plasma membrane derived microvesicles, by incubation with a reactant, consisting of at least a membrane anchor domain or moiety and a hydrophilic functional domain or moiety. The invention also relates to modification using the same of artificially-prepared lipid bilayer vesicles called liposomes (composed of natural phospholipids) and non-biological or "synthetic" block copolymer membrane mimics which also form vesicles in aqueous solution called polymersomes.

15 Claims, 1 Drawing Sheet

(56) References Cited

FOREIGN PATENT DOCUMENTS

| | | |
|---|---|---|
| WO | 2009100029 A1 | 8/2009 |
| WO | 2009127537 A1 | 10/2009 |
| WO | 2011009104 A1 | 1/2011 |

OTHER PUBLICATIONS

Brugger et al., Human Immunodeficiency Virus Type 1 Nef protein modulates the lipid composition of virions and host cell membrane microdomains. Retrovirology. Oct. 1, 2007;4:70 (12 pages).

Campbell et al., A monomeric red fluorescent protein. Proc Natl Acad Sci U S A. Jun. 11, 2002;99(12):7877-7882.

Campbell, Unit Three: The Gene.in Biology. Redwood City, CA: Benjamin/Cummings Publishing Company, Inc., 1993:350-351 (4 pages total).

Chan et al., Conjugation of Lentivirus to Paramagnetic Particles via Nonviral Proteins Allows Efficient Concentration and Infection of Primary Acute Myeloid Leukemia Cells. J Virol. Oct. 2005;79(20):13190-13194.

Cheruvanky et al., Rapid isolation of urinary exosomal biomarkers using a nanomembrane ultrafiltration concentrator. Am J Physiol Renal Physiol. May 2007;292(5):F1657-F1661.

Clayton et al., Antigen-presenting cell exosomes are protectedfrom complement-mediated lysis by expression ofCD55 and CD59. Eur J Immunol. Feb. 2003;33(2):522-531.

International Search Report issued in PCT/EP2013/071366 dated Apr. 16, 2014 (6 pages).

Hlavaty et al., Multiple Modifications Allow High-Titer Production of Retroviral Vectors Carrying Heterologous Regulatory Elements. J Virol. Feb. 2004;78(3):1384-1392.

Ikeda et al., Continuous high-titer HIV-1 vector production. Nat Biotechnol. May 2003;21(5):569-572.

Ilangumaran et al., Transfer of exogenous glycosylphosphatidylinositol (GPI)-linked molecules to plasma membranes. Trends Cell Biol. May 1996;6(5):163-167.

Ito et al., Medical Application of Functionalized Magnetic Nanoparticles. J Biosci Bioeng. Jul. 2005;100(1):1-11.

Jordan et al., The effect of thermotherapy using magnetic nanoparticles on rat malignant glioma. J Neurooncol. May 2006;78(1):7-14.

Keler et al., Antibody-targeted vaccines. Oncogene. May 28, 2007;26(25):3758-3767.

Klein et al., Rapid identification of viable retrovirus-transduced cells using the green fluorescent protein as a marker. Gene Ther. Nov. 1997;4(11):1256-1260.

Kueng et al., General Strategy for Decoration of Enveloped Viruses With Functionally Active Lipid-Modified Cytokines. J Virol. Aug. 2007;81(16):8666-8676.

Legler et al., Differential insertion of GPI-anchored GFPs into lipid rafts of live cells. FASEB J. Jan. 2005;19(1):73-75.

Lim et al., Immobilization of histidine-tagged proteins by magnetic nanoparticles encapsulated with nitrilotriacetic acid (NTA) phospholipids micelle. Biochem Biophys Res Commun. Jun. 9, 2006;344(3):926-930.

McHugh et al., Construction, purification, and functional incorporation on tumor cells of glycolipid-anchored human B7-1 (CD80). Proc Natl Acad Sci U S A. Aug. 15, 1995;92(17):8059-8063.

Medof et al., Cell-surface engineering with GPI-anchored proteins. FASEB J. Apr. 1996;10(5):574-586.

Metzner et al., Association of glycosylphosphatidylinositol-anchored protein with retroviral particles. FASEB J. Aug. 2008;22(8):2734-2739.

Metzner et al., Rafts, anchors and viruses—A role for glycosylphosphatidylinositol anchored proteins in the modification of enveloped viruses and viral vectors. Virology. Dec. 20, 2008;382(2):125-131.

Morandat et al., Cholesterol-dependent insertion of glycosylphosphatidylinositol-anchored enzyme. Biochim Biophys Acta. Aug. 31, 2002;1564(2):473-478.

Nagrath et al., Isolation of rare circulating tumour cells in cancer patients by microchip technology. Nature. Dec. 20, 2007;450(7173):1235-1239.

Pambalk et al., Specific packaging of spliced retroviral vector transcripts lacking the Psi-region. Biochem Biophys Res Commun. Apr. 26, 2002;293(1):239-246.

Paulick et al., Synthetic Analogues of Glycosylphosphatidylinositol-Anchored Proteins and Their Behavior in Supported Lipid Bilayers. J Am Chem Soc. Sep. 19, 2007;129(37):11543-11550.

Pessin et al., Budding of Rous Sarcoma Virus and Vesicular Stomatitis Virus from Localized Lipid Regions in the Plasma Membrane of Chicken Embryo Fibroblasts. J Biol Chem. Oct. 10, 1980;255(19):9044-9050.

Premkumar et al., Properties of Exogenously Added GPI-Anchored Proteins Following Their Incorporation Into Cells. J Cell Biochem. 2001;82(2):234-245.

Raposo et al., B Lymphocytes Secrete Antigen-Presenting Vesicles. J Exp Med. Mar. 1, 1996;183(3):1161-1172.

Rohrbach et al., Targeted Delivery of the ErbB2/HER2 Tumor Antigen to Professional APCs Results in Effective Antitumor Immunity. J Immunol. May 1, 2005;174(9):5481-5489.

Ronzon et al., Insertion of a Glycosylphosphatidylinositol-Anchored Enzyme into Liposomes. J Membr Biol. Feb. 1, 2004;197(3):169-177.

Roux et al., A versatile and potentially general approach to the targeting of specific cell types by retroviruses: application to the infection of human cells by means of major histocompatibility complex class I and class II antigens by mouse ecotropic murine leukemia virus-derived viruses. Proc Natl Acad Sci U S A. Dec. 1989;86(23):9079-9083.

Saifuddin et al., Human immunodeficiency virus type 1 incorporates both glycosyl phosphatidylinositol-anchored CD55 and CD59 and integral membrane CD46 at levels that protect from complement-mediated destruction. J Gen Virol. Aug. 1997;78 ( Pt 8):1907-1911.

Schevchenko et al., Mass Spectrometric Sequencing of Proteins from Silver-Stained Polyacrylamide Gels. Anal Chem. Mar. 1, 1996;68(5):850-858.

Shaw et al., Cellular Proteins in Influenza Virus Particles. PLoS Pathog. Jun. 6, 2008;4(6):e1000085.

Skog et al., Glioblastoma microvesicles transport RNA and proteins that promote tumour growth and provide diagnostic biomarkers. Nat Cell Biol. Dec. 2008;10(12):1470-1476.

Skountzou et al., Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles. J Virol. Feb. 2007;81(3):1083-1094.

Steinrigl et al., Mutations in the catalytic core or the C-terminus of murine leukemia virus (MLV) integrase disrupt virion infectivity and exert diverse effects on reverse transcription. Virology. May 25, 2007;362(1):50-59.

Sullivan-Tailyour et al., Plasma Membrane Proteins and Glycoproteins Induced by Human Cytomegalovirus Infection of Human Embryonic Fibroblasts. J Gen Virol. Mar. 1986;67 ( Pt 3):515-526.

Taraboletti et al., Bioavailability of VEGF in Tumor-Shed Vesicles Depends on Vesicle Burst Induced by Acidic pH1. Neoplasia. Feb. 2006;8(2):96-103.

Taylor and Gercel-Taylor, MicroRNA signatures of tumor-derived exosomes as diagnostic biomarkers of ovarian cancer. Gynecol Oncol. Jul. 2008;110(1):13-21.

Thery et al., Exosomes: composition, biogenesis and function. Nat Rev Immunol. Aug. 2002;2(8):569-579.

Thery et al., Isolation and Characterization of Exosomes from Cell Culture Supernatants and Biological Fluids. Curr Protoc Cell Biol. Apr. 2006;Chapter 3:Unit 3.22.

Wilhelm et al., Tumour Cell Toxicity of Intracellular Hyperthermia Mediated by Magnetic Nanoparticles. J Nanosci Nanotechnol. Aug. 2007;7(8):2933-2937.

Yang et al., Engineered Lentivector Targeting of Dendritic Cells for In Vivo Immunization. Nat Biotechnol. Mar. 2008;26(3):326-334.

Yang et al., Gamma-Retroviral Vectors Enveloped with an Antibody and an Engineered Fusogenic Protein Achieved Antigen-Specific Targeting. Biotechnol Bioeng. Oct. 1, 2008;101(2):357-368.

(56) References Cited

OTHER PUBLICATIONS

Yang et al., Targeting lentiviral vectors to specific cell types in vivo. Proc Natl Acad Sci U S A. Aug. 1, 2006,103(31):11479-11484.
Zacharias et al., Partitioning of Lipid-Modified Monomeric GFPs into Membrane Microdomains of Live Cells. Science. May 3, 2002;296(5569):913-916.
Zacharias, Sticky Caveats in an Otherwise Glowing Report: Oligomerizing Fluorescent Proteins and Their Use in Cell Biology. Sci STKE. May 7, 2002;2002(131):pe23.
Ziegler et al., Targeting Lentiviral Vectors to Antigen-Specific Immunoglobulins. Hum Gene Ther. Sep. 2008;19(9):861-872.

METHOD OF PAINTING MICRO VESICLES

CROSS-REFERENCE TO RELATED APPLICATIONS

The present invention is a Continuation-in-Part application of U.S. application Ser. No. 14/432,998, filed Apr. 1, 2015, which is the U.S. national phase of International Patent Application No. PCT/EP2013/071366, filed Oct. 11, 2013, which designated the U.S. and claims the benefit of priority to U.S. Provisional Application No. 61/712,471, filed on Oct. 11, 2012; and is a Continuation-in-Part application of U.S. application Ser. No. 14/860,107, filed Sep. 21, 2015, which is a continuation of U.S. patent application Ser. No. 12/988,046, filed Dec. 7, 2010, now U.S. Pat. No. 9,139,817, issued Sep. 22, 2015, which is the U.S. national phase of International Patent Application No. PCT/EP2009/054016, filed Apr. 3, 2009, which claims the benefit of priority to European Patent Application No. 08154748.1 filed Apr. 17, 2008, each of which is incorporated by reference in their entirety for all purposes, including all tables, figures and claims.

FIELD OF THE INVENTION

The present invention relates to a method to modify and/or to isolate exosomes and other naturally occurring plasma membrane derived microvesicles, by incubation with a reactant, consisting of at least a membrane anchor domain or moiety and a hydrophilic functional domain or moiety. The invention also relates to modification using the same of artificially-prepared lipid bilayer vesicles called liposomes (composed of natural phospholipids) and non-biological or "synthetic" block copolymer membrane mimics which also form vesicles in aqueous solution called polymersomes. All of the membrane based vesicles (natural or synthetic) that relate to this membrane modifying invention will be broadly termed as membrane microvesicles (MMV) for the purpose of description in this application. The hydrophilic functional domain of the membrane modifying element carries a tag, which allows for example a consequent location or separation of the vesicles after the incubation step during which the vesicles are "painted". Such "molecular painting" (MP) therefore describes the surface modification with the described molecule which then allows for further and diverse downstream functionalities and applications due to the molecule itself and/or the included tag (dual-functionality). By exogenously altering the composition of MMV membranes via introducing such a tagged molecule by MP, for example via a GPI-(glycosyl-phosphatidyl-inositol) anchor, these can then be used for a variety of downstream applications such as targeting of drug or gene delivery MMV (since targeting molecules can be added to their outer membrane) or in diagnostics as they can easily isolated from the rest of the sample due to the MP membrane tag.

Further the invention relates to the use of such reactants to alter MMV membranes by MP for medical, biotechnological, research or diagnostic purposes. More specifically, basic and applied research, laboratory and hospital diagnostics, use with exosome or other MMV based biomarkers (research and medically), vaccine development, targeting and delivery of genes proteins and/or drugs and gene therapy. Because this modification is of a general type, the method allows the universal MP-based surface modification of all—even so far unknown—MMV and thereby facilitates the discovery of more so far unknown types of MMV.

SUMMARY OF THE INVENTION

The present invention relates to a method to modify and/or to isolate exosomes and other naturally occurring plasma membrane derived microvesicles, by incubation with a reactant, consisting of at least a membrane anchor domain or moiety and a hydrophilic functional domain or moiety. The invention also relates to modification using the same of artificially-prepared lipid bilayer vesicles called liposomes (composed of natural phospholipids) and non-biological or "synthetic" block copolymer membrane mimics which also form vesicles in aqueous solution called polymersomes. All of the membrane based vesicles (natural or synthetic) that relate to this membrane modifying invention will be broadly termed as membrane microvesicles (MMV) for the purpose of description in this application. The hydrophilic functional domain of the membrane modifying element carries a tag, which allows for example a consequent location or separation of the vesicles after the incubation step during which the vesicles are "painted". Such "molecular painting" (MP) therefore describes the surface modification with the described molecule which then allows for further and diverse downstream functionalities and applications due to the molecule itself and/or the included tag (dual-functionality). By exogenously altering the composition of MMV membranes via introducing such a tagged molecule by MP, for example via a GPI-(glycosyl-phosphatidyl-inositol) anchor, these can then be used for a variety of downstream applications such as targeting of drug or gene delivery MMV (since targeting molecules can be added to their outer membrane) or in diagnostics as they can easily isolated from the rest of the sample due to the MP membrane tag.

Further the invention relates to the use of such reactants to alter MMV membranes by MP for medical, biotechnological, research or diagnostic purposes. More specifically, basic and applied research, laboratory and hospital diagnostics, use with exosome or other MMV based biomarkers (research and medically), vaccine development, targeting and delivery of genes proteins and/or drugs and gene therapy. Because this modification is of a general type, the method allows the universal MP-based surface modification of all—even so far unknown—MMV and thereby facilitates the discovery of more so far unknown types of MMV.

BACKGROUND OF THE INVENTION

Figure 1:
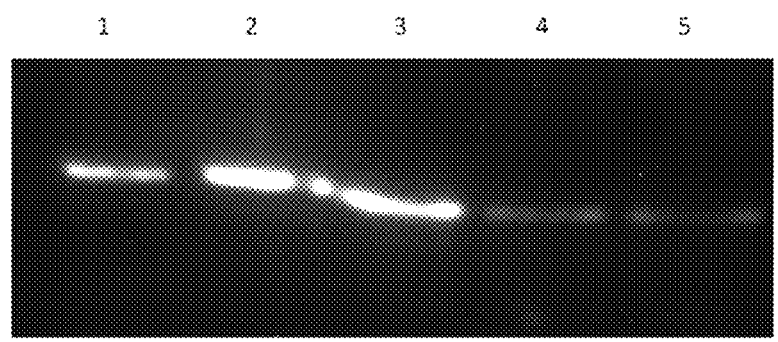
FIG. 1 shows a photograph taken from the Western-Blot of the membrane that was incubated with the exosome specific antibody anti-PDC6I. The numbers are indicating the lanes that were used and they correspond to the samples prepared (sample 1 in lane 1 etc.).

Membrane microvesicles (MMV) (sometimes called circulating microvesicles, or microparticles) are fragments of phospholipid bilayer plasma membrane ranging from 30 nm to 1000 nm shed from almost all cell types. MMV, therefore are a subtype of membrane-vesicles, and play a role in intercellular communication and can deliver mRNA, siRNA, and proteins between cells. They have been implicated in the process of cancer tumour immune suppression, metastasis, tumor-stroma interactions and angiogenesis along with having a role in tissue regeneration. They originate directly from the plasma membrane of the cell and reflect the antigenic content of the cells from which they originate.

Exosomes are vesicles of 30-100 nm in diameter, which are actively secreted by a wide range of mammalian cell types under both normal and pathological conditions. Exosomes can be regarded as a sub-class of MMV. First discovered in maturing mammalian reticulocytes, they were shown to be a mechanism for selective removal of many plasma membrane proteins and to discard transferrin-receptors from the cell surface of maturing reticulocytes. Although the exosomal protein composition varies with the cell of origin, most exosomes contain the soluble protein Hsc 70 and many others. 31 proteins are found to be in common between colorectal cancer, mast cells and urine-derived exosomes. Certain cells of the immune system, such as dendritic cells and B cells, secrete exosomes that many scientists believe play a functional role in mediating adaptive immune responses to pathogens and tumours.

Exosomes may be formed through inward budding of endosomal membranes giving rise to intracellular multivesicular bodies (MVB) that later fuse with the plasma membrane, releasing the exosomes to the exterior (Thery et al. (2002) Exosomes: composition, biogenesis and function. Nat Rev Immunol. 2:569-79.). In other words, an exosome is created intracellularly when a segment of the cell membrane spontaneously invaginates and is endocytosed. The internalized segment may be broken into smaller vesicles that are subsequently expelled from the cell. The latter stage occurs when the late endosome, containing many small vesicles, fuses with the cell membrane, triggering the release of the vesicles from the cell. The vesicles (once released may be called exosomes) consist of a lipid raft embedded with ligands common to the original cell membrane.

However, a more direct release of exosomes has been described by Booth et al. (2006), Jurkat T-cells, are said to shed exosomes directly by outward budding of the plasma membrane.

Exosomes secreted by cells under normal and pathological conditions contain proteins and functional RNA molecules including mRNA and siRNA, which can be shuttled from one cell to another, affecting the recipient cell's protein production. This RNA is called "exosomal shuttle RNA". Exosomes can also be released into urine by the kidneys and their detection might serve as a diagnostic tool. Urinary exosomes may be useful as treatment response markers in prostate cancer. Exosomes released from tumours into the blood can be used diagnostically.

Because exosomes carry RNA from the cell it was released from, it may be possible that they carry DNA as well. By employing a specific mRNA as biomarker Skog, et al. (2008) showed that tumour mutations in brain tumours can be detected in exosomes from a serum sample, facilitating a blood-based biomarker platform for solid tumours.

In WO/2009/100029 a method for aiding in the diagnosis or monitoring of a disease is described, which comprises the steps of obtaining a biological sample, such as a bodily fluid from the subject; and isolating therefrom the MMV of interest.

Methods of isolating MMV from a biological sample are known in the art. For example, a method of differential centrifugation is described in a paper by Raposo et al. (1996).

A method of magnetic activated cell sorting (MACS) has been described by Taylor and Gercel-Taylor in 2008). Magnetic-activated cell sorting (MACS) is a trademark name for a method for separation of various cell populations depending on their surface antigens. Magnetic cell separation using antibodies is also possible using mono-sized magnetic beads (Dynabeads) from Invitrogen (now part of Life Technologies). The Dynabeads technology is not column based, instead these magnetic beads with attached cells enjoy liquid phase kinetics in a sample tube, and the cells are isolated by placing the tube on a magnetic rack.

An MMV fraction, such as the exosomes, may also be isolated from the bodily fluid sample by affinity purification, filtration concentration, affinity chromatography, ion exchange, and any combination of any of the foregoing. A method of nanomembrane ultrafiltration concentrator has been described by Cheruvanky et al. (2007). It has also been described that the MMV fraction may be concentrated by passing the biological sample through a filter having a pore size of less than or equal to 0.8 µm (WO/2011/009104). Due to their small size and characteristic density exosomes are usually purified via ultracentrifugation (Thery et al. (2006)).

Each of the foregoing references is incorporated by reference herein for its teaching of these methods.

However, none of the methods is able to enrich for enveloped viruses as well as MMV, such as exosomes or bigger, simultaneously. That is because the methods known in the art are either based on purifying everything in the sample by density or size (e.g. filters or ultracentrifugation) or limited to purifying only the elements that specifically react with the antibody being used, meaning that the purification is limited to molecules that have been previously identified and had antibodies generated for.

Furthermore, none of these isolation methods provides the same advantages for labelling MMV, such as exosome, as the methods according to the invention. For example, ultracentrifugation causes sheer stresses to vesicles (and viruses) during both the centrifugation and resuspension from pellet stages. Filters are an unknown factor because there are always unknown interactions between the sample elements and the filter materials so it can never be determined what is being lost, especially when the target is novel or unknown, e.g. when researching on new infectious agents or identifying new diagnostic markers.

The isolation of MMV from specific cell types can be accomplished, for example, by using cell type specific antibodies, aptamers, aptamer analogues or molecularly imprinted polymers specific for a desired surface antigen. The surface antigen may be specific for a cancer type, or the surface antigen may be specific for a cell type which is not necessarily cancerous. One example of a method of MMV separation based on cell surface antigen is provided in U.S. Pat. No. 7,198,923. As described in, e.g., U.S. Pat. Nos. 5,840,867 and 5,582,981, WO/2003/050290, aptamers and their analogues specifically bind surface molecules and can be used as a separation tool for retrieving cell type-specific MMV.

Molecularly imprinted polymers also specifically recognize surface molecules as described in, e.g., U.S. Pat. Nos. 6,525,154, 7,332,553 and 7,384,589 and are another tool for retrieving and isolating cell type-specific MMV.

MMV can also be identified and isolated from bodily fluid of a subject by a microchip technology that uses a microfluidic platform to separate tumour derived MMV. This technology, as described in a paper by Nagrath et al. (2007), has been adapted to identify and separate MMV using similar principles of capture and separation as taught in the paper. To quantify and profile exosomes from plasma this multiplexed platform uses antibodies, that are specific to membrane proteins for: exosomes generally (Alix, TSG101 and the tetraspanin proteins CD81 and CD9 and also CD63 are characteristic exosome markers), exosomes from prostate epithelial cells (PSMA and PCSA), and tumour-associated exosomes (EpCam and B7H3). These seven surface membrane protein biomarkers were captured and detected in the exosome membrane by antibodies. Because the MMV often carry surface molecules such as antigens from their donor cells, surface molecules may be used to identify, isolate and/or enrich for MMV from a specific donor cell type.

Each of the foregoing reference is incorporated herein for its teaching of these methods.

The prior art furthermore comprises the use of dyes, such as cyanine dyes to stain cell membranes (for example U.S. Pat. No. 4,783,401). And it has recently been reported that such dyes were used to label MMV (in WO/2009/100029, Example 17). To demonstrate that glioblastoma MMV are able to be taken up by human brain microvesicular endothelial cells (HBMVECs), purified glioblastoma MMV were labelled with a Green Fluorescent labelling kit, which basically provides a cyanine dye. It's mode of action is based on the dye having sufficient lipid solubility to enter membranes unspecifically. Hence the staining would allow staining all types of membranes in the sample. This approach allows visualisation of membranes, membranes of cells as well as of membrane vesicles, but does not provide the means to tag the vesicles in such a way, that the staining does not allow to physically separate the labelled membrane particles from their surrounding environment.

This however has been overcome by the substances and methods according to the invention. The possibility to tag the membrane-vesicles with a reactant according to the invention enables an easy separation and/or purification thereof.

A typical cellular transport pathway makes use of a glycosylphosphatidylinositol (GPI) anchor to direct proteins and polypeptides to the outer leaflet of cell membranes. GPI anchors are attached to protein precursors at the endoplasmic reticulum (ER) membrane by a transamidase enzyme complex and delivered to the outer leaflet of the plasma membrane. GPI-linked proteins serve different functions i.e. in the regulation of complement activity (e.g. CD59; CD55) or as hydrolytic enzymes (e.g. alkaline phosphatase or renal dipeptidase). GPI anchors consist of a hydrophilic oligosaccharide and a lipophilic fatty acid part. Unlike conventional polypeptide anchors, which have different transmembrane sequences and connect to specific cytoplasmic extensions, these phospholipid-like anchors use a common structure as a general mechanism for membrane attachment irrespective of protein function.

It has further been demonstrated that GPI anchors can be added to previously non-GPI-linked proteins (e.g. green fluorescent protein (GFP) by genetically based addition of a GPI signalling sequence (GSS) to their C-terminal end and that these proteins retain their biological functions.

Basically any proteins can be expressed as GPI-anchored protein, and both, naturally occurring and artificially generated GPI-anchored proteins can be purified and re-inserted into the cell membranes The extracellular use of such GPI-anchored proteins to label cell membranes has been described by Medof (Medof et al. (1996) Cell-surface engineering with GPI-anchored proteins. FASEB J. 10:574-586), who thereby presented an alternative to the so far used technology of amending the cell surface by endogenous alteration of the membrane, i.e. via genetic transfer with GPI coding sequences. He termed the process of exogenous insertion of substances like proteins into cell membranes via GPI anchors as "cell painting". Also in 1996, Ilangumaran et al. reported that GPI-linked molecules can incorporate spontaneously in vitro into mammalian cell plasma membranes. Transfer of GPI-linked proteins between cells has also been documented in vivo.

It has also been reported that enveloped virus particles, may be painted with GPI-like proteins.

Metzner et al. have reported upon a method on how to tag viral particles exogenously with GPI-like anchored proteins, in other words without the need for genetic engineering of virus producer cell lines (PCT application WO/2009/127537) and this was termed "virus painting". In viruses it could be shown that the virus envelopes were labelled successfully without reducing the virus' infectivity.

The inventors found that surprisingly also MMV, such as exosomes and polymersomes can be painted with said GPI-anchored protein tags. They realized the potential of this type of painting to tag the MMV membranes, and to use this tag for purification, isolation, concentration or enriching of the membrane vesicles, such as exosomes, which at the same time fully remain their biological function. The methods according to the invention therefore employ the painting technique with GPI-like molecules to purify, isolate, concentrate or enrich for MMV, including exosomes. As such they have termed the painting of all MMV, cells and viruses as "Molecular Painting" (MP).

A pool of sophisticated methods to isolate, purify or concentrate specific MMV is known in the art. However these are not suitable to identify new MMV of unknown surface proteins, but limited to isolate or detect those with a known protein or antigen exposed on their surface.

It has been suggested to use affinity filtration, affinity centrifugation, affinity chromatography or magnetic activated cell sorting by employing antibodies, against antigens that are apparently common to all exosomes, and are therefore supposed to be characteristic for exosomes. There might however be other MMV, or other exosomes in the bodily fluids, which do not express any of these antigens or exosome marker proteins. These MMV would never be detected with a method based on affinity. In addition, all of these affinity based methods require the use of antibodies, which is expensive and cumbersome.

Alternative methods that do not use antibodies are for example, isolation by centrifugation, ultracentrifugation, or centrifugation of a chromatography fraction, wherein the chromatography does not rely on affinity mediated by an antibody, but for example on size exclusion.

Conventional methods to prepare membrane vesicles e.g. exosomes involve a series of differential centrifugation steps to separate the vesicles from cells or cell debris present in the culture medium. Essentially vesicles may be isolated with a series of centrifugations at 300 g, 10,000 g and 70,000 g or 100,000 g, the pellet obtained being taken up with a saline solution to constitute a concentrated exosome solution. This preparation may be analysed using conventional biochemical techniques used to evaluate the protein composition of the exosomes.

A preferred biochemical technique consists of electrophoresis in a denaturing medium combined with staining of the total proteins or the detection of specific proteins using antibodies according to the Western Blot technique. The exosomes in the final preparation may be detected directly by electron microscopy after fixing the preparation with a 4% glutaraldehyde solution.

Alternative methods of anion exchange and/or gel permeation chromatography and size exclusion chromatography have been described in U.S. Pat. Nos. 6,899,863 and 6,812,023.

All these methods carry potential disadvantages. Centrifugation processes do not enable the fine separation of membrane vesicles (e.g. exosomes) from cell proteins or certain macromolecular components (DNA, RNA) or macromolecular complexes. Therefore, these processes do not exclude the presence of unidentified contaminating biological agents, incompatible with therapeutic use in humans. In addition, these steps are difficult to extrapolate at an industrial scale, particularly when significant volumes are to be treated, or for autologous (i.e. patient by patient) ex vivo applications, in which the process must generally be applied in a confined system.

The use of ultracentrifugation could solve some of the problems, but increases the price of the isolation step significantly, making it unsuitable for a large percentage of laboratories who do not possess the equipment, and makes it unsuitable for high-through-put methods, which is a requirement for an affordable diagnostic tool.

Therefore, there is a need in the art to isolate, purify, concentrate, or enrich for and capture MMV per se, in order to identify new types of MMV, especially exosomes, with so far unknown marker molecules, in a fast and efficient way, without adversely affecting the morphology or function of the MMV.

In addition there is—to our knowledge—no method known in the art to isolate and label two different types of vesicles, such as any type of MMV and enveloped virus, simultaneously. This however is achieved by a method according to the invention, and brings a distinct advantage when developing a diagnostic kit or tool which aims to screen for multiple infectious agents or disease states simultaneously using one extraction protocol with one sample, thereby saving on sample material and thereby reducing the amount of sample that needs to be taken (for diagnostic purposes). Currently, the best technology available (other than ultracentrifugation) would require the use of multiple antibodies, specific for every vesicle or virus that could potentially be present in the sample. This is costly, time consuming and most importantly would require large amounts of sample, which in most diagnostic scenarios, is not available.

The methods according to the invention overcome these shortages, because the inventors found that surprisingly MMV, such as exosomes can be painted with tagged GPI-anchored proteins. This finding is particularly surprising since, in contrast to well defined enveloped virus particles, MMV show a high degree of diversity and differences in terms of their origin, method of synthesis (natural and/or synthetic), size and membrane composition, including unknown natural or synthetic components, for example, sphingolipids or proteins or carbohydrates and therefore it would have not been reasonable to assume that molecular painting (MP) would work. In contrast to this, the inventors realized the potential of this type of MP to tag the MMV membranes, and to use this tag for purification, isolation, concentration or enriching of the membrane vesicles, such as exosomes, which at the same time fully remain their biological function. The methods according to the invention therefore employ the MP technique with GPI-like molecules to purify, isolate, concentrate or enrich for MMV, including exosomes.

DETAILED DESCRIPTION OF THE INVENTION

The methods according to the invention are for modifying the membranes of MMV, and for isolating, purifying, concentrating of or enriching for such membrane modified MMV and optionally detecting and/or identifying them afterwards. It is preferred that these MMV are exosomes, liposomes or polymersomes.

Furthermore a method according to the invention allows to simultaneously enrich for enveloped viruses as well as MMV, such as exosomes or bigger.

Surprisingly, the incubation, or in other words the MP step, works even without having to isolate the MMV first. Hence, there is no need to isolate the MMV from the sample before incubating it with the reactant, in order to still achieve a sufficient MP reaction of the exosomes.

Various aspects and embodiments of the invention will now be described in detail. It will be appreciated that modification of the details may be made without departing from the scope of the invention. Further, unless otherwise required by context, singular terms shall include pluralities and plural terms shall include the singular.

Definitions

All membrane vesicles of a size of 20-1000 nm in diameter shed by cells (derived from the plasma membrane) are referred to herein collectively as "membrane microvesicles" or MMV. The invention relates to the molecular painting (MP) of all natural and synthetic membrane-related membrane microvesicles (MMV). It is a preferred embodiment of the invention wherein the MMV are exosomes, liposomes or polymersomes.

Wherein the term "isolating" is used to describe a step in a method according to the invention the scope of the term is understood to comprise the meanings of "purifying", "concentrating" and "enriching for".

A "reactant" according to the present invention is a substance which is capable of inserting or integrating itself into lipid double layers, especially of membranes of MMV. A reactant according to the invention consists of at least two distinct parts: (a) a membrane anchor domain or moiety and, (b) a hydrophilic target domain or moiety to be exposed to the outside of the MMV. Such reactants may contain further parts, providing for additional physical or chemical properties or to allow for linkage to other chemicals, proteins or organic or non-organic, magnetic or non-magnetic materials such as microparticles, nanoparticles, beads, affinity or filter materials. Reactants contain herein defined extraction (EX)-tags, usually protein-tags, such as the histidine tag and/or flag-tag for example, which enable the extraction of the tagged vesicles and are essential for the purification of said reactants or for purification and/or concentration of MMV modified with said reactants. Hence for definition purposes in this application the term "EX" relates to any such tag which can potentially provide such functionality. The attaching of the EX-tag to the MMV is therefore an essential element of the invention.

The term reactant may also, in a preferred embodiment, refer to the complex substance consisting of a membrane anchor domain, comprising of a lipophilic part, which interacts with or rather penetrates into the MMV membranes, and a hydrophilic part, which is covalently joined to a hydrophilic target domain carrying an EX-tag, which according to the invention, enables the isolation of MMV that are attached to the lipophilic part of the membrane anchor domain, preferably by extracting them from a solution.

It is a preferred embodiment that the EX-tag itself is attached to a magnetic bead, while incubating with the vesicles. In another embodiment the reactant may be attached or bound via said EX-tag to a metal chelate membrane absorbers (such as Ni affinity filter) or column, thereby combining the incubation and isolation step, into one step.

The term "EX-tag" according to the invention refers to a tag, that may be a protein or peptide tag, such as a for example a Histidine-tag (His-tag), or other single or several amino acid(s). In some embodiments these can be chemically modified to allow attachment of a second peptide or protein tag or bioactive molecule, or a chemical entity or an organic or non-organic micro- or nano- or bead or related type of particle, characterised as enabling the extraction or isolation of the so-tagged MMV (or enveloped virus particle).

"Exogenous modification" in the context of the present invention means that the reactants to be inserted into the membrane are added to MMV, such as for example exosomes, outside of a cell, or in absence of a cell, in an appropriate suspension medium. Such a medium could be a bodily fluid sample, a preconditioned bodily fluid sample, buffered saline or cell culture medium e.g. DMEM. The presence of a cellular host is not necessary for the process/technology. The method is termed "molecular painting".

"Membrane anchor domains or moieties" are amphiphilic molecules which are able to integrate into lipid double layers with their lipophilic part, whereas the hydrophilic part is exposed to the surrounding watery or aqueous medium. The hydrophobic group is typically a large hydrocarbon moiety, such as a long chain of the form $R=CH_3(CH_2)_n$, with $n>4$ or a cyclic hydrocarbon moiety. The hydrophilic group can either be charged or polar, uncharged groups. Charged groups are e.g. carboxylates: $RCO_2^-$; sulfates: $RSO_4^{2-}$; sulfonates: $RSO_3^-$; phosphates (the typical charged functionality in phospholipids), carbohydrates or amines $RNH_3^+$. Polar, uncharged groups are alcohols with large R groups, such as diacyl glycerol (DAG), and oligoethyleneglycols with long alkyl chains. Some amphiphilic membrane anchor domains like GPI have several hydrophobic parts, several hydrophilic parts, or several of both.

Preferred membrane anchor domains according to the methods of the invention are phospholipid-polyethylene glycol, stearyl, cholesterol, chelator lipid, nitrilotriacetic acid ditetradecylamine (NTA-DTDA), farnesyl, myristyl or palmitoyl moieties. Most preferred are glycosylphosphatidylinositol (GPI) or analogues thereof. According to the invention the glycosylphosphatidylinositol (GPI) is a preferred amphiphilic membrane anchor domain, which consists of (a) a molecule of phosphatidylinositol, which carries the long chain fatty acids and therefore may be described as the lipophilic part, (b) a glycan core, and (c) a phosphoethanolamine moiety, which may be described as the hydrophilic part of the membrane anchor domain. Hydrophilic target domains are covalently bound (if they are proteins usually via their C-terminus) to the phosphoethanolamine, and as such to the hydrophilic part of the membrane anchor.

"Analogues" are mimics of GPI anchor domains wherein portions of the glycan core are systematically replaced with synthetic linkers of comparable length and dimension. The analogues might contain no, one or two mannose units and replace the phosphoinositol and glucosamine units with a simple hydrophilic poly(ethylene glycol) linker which allows for the installation of various side chains and different lipid tails. Examples are given in Paulick et al (2007) which is incorporated herein by reference.

"Hydrophilic target domains or target moieties" according to the present invention are covalently joined to the hydrophilic part of membrane anchor domains. Target domains are preferably proteins or polypeptides, herein also named target proteins e.g. enzymes, antigen recognition sides, receptors, protein markers, fluorescence markers or proteins, or peptide hormones or cytokines. Such target domains may be further modified by joining of protein tags and/or peptide tags and/or other functional groups (e.g. biotinyl residues, cross linkers, carbohydrates) to them. Alternatively these tags may be attached or bound to the hydrophilic part of the anchor domain itself, in which case the tag itself becomes said hydrophilic target domain.

A preferred target domain protein according to the invention is the enhanced green fluorescent protein (eGFP) or red fluorescent protein (RFP) and their variants (e.g. YFP), especially the monomeric forms. CD59 or CD55 are preferred as reactants or part of the reactants as they naturally consist of a membrane anchor domain (namely a GPI) as well as a target protein (functional protein).

Non-protein target domains could be e.g. polysaccharides, nucleic acids, dyes, radioactive ligands, or fluorescent dyes. Even more complex structures like polystyrol beads or (nano)magnetic particles may be joined to a membrane anchor domain, for example via a his tag and the hydrophilic target domain, or via the tag itself.

In the following the term "exosome" is understood to be a particularly small MMV, as has been explained in more detail above.

In the following the term "incubating" is understood as allowing two or more reagents, liquids or substances or mixtures thereof to interact with each other, under varying conditions. The incubation step according to the invention may be performed at final concentrations of between 35 ng/ml and 35 mg/ml (preferably 35 µg/ml) of the afore defined reactant to be mixed together with afore defined MMV and/or viruses. It is preferred that the incubation is performed during vigorous shaking and mixing, which however does not reach the intensity of a vibrational or vortex stirring. This mixing movement may be performed for a period between 10 seconds and 48 hours. A preferred time of shaking is 10 min-1 h, and most preferred is a shaking time of 30 minutes. The temperature during the incubation is between 4 and 60 degrees Celsius, preferably between 20 and 40 degrees Celsius and most preferably at 35-39 degree Celsius.

An "enveloped virus" or "enveloped viral particle" is a virus which exhibits a viral envelope. A viral envelope typically has a protein to lipid mole fraction expressed in mole percentage (mol %) between 50 and 90, preferably 65 to 85 and most preferably 70 to 80. The term "enveloped virus" or "enveloped viral particle" according to the present invention comprises different taxonomic families, which can be divided in corresponding subfamilies, genus and species. An "enveloped virus" can be selected from any group of family, subfamily, genus or species.

The inventors disclose herein a new method to isolate and identify a MMV fraction by employing reactants that comprise a lipophilic membrane anchoring domain and a hydrophilic target domain, such as GPI-linked proteins, to modify the MMV outer surface, or rather the vesicles' membranes, thereby providing a painting, tagging or labeling of all MMV, including exosomes, independent of their protein constitution at the outer surface of the vesicle membrane. The method is characterised therein that the hydrophilic part of the reactant which is exposed to the surrounding environment of the MMV carries a certain type of tag, such as a peptide or protein tag, which can be used to isolate the MMV it is attached to.

The method is based on a reaction between a molecule referred to as the reactant, which preferably is a GPI-anchored protein, and the MMV membrane. That way it is ensured that indeed all membrane vesicles will be tagged. Because the method according to the invention is based on a general mode of action of the insertion of glycosyl-phosphatidyl-inositol-like anchored molecules into the membranes of all MMV, there is no limitation of the method as to certain types of MMV that do express specific surface molecules. By incubating the MMV, which preferably are exosomes, with a reactant which comprises a lipophilic membrane anchoring domain and a hydrophilic target domain and/or a protein or peptide tag, all the MMV are now tagged. As a result of this or as a result of the tag being attached to this hydrophilic target domain, they can easily be isolated or purified from the reaction mix.

It is also a preferred embodiment wherein the tag at the reactant, whether bound to the amphiphilic membrane anchor domain, or bound to the hydrophilic target domain, has magnetic beads attached to it. Hence while incubating the MMV in the sample with that type of reactant; the magnetic beads are attached to the vesicles membranes in a one-step reaction. In another embodiment the Ex-tag facilitates the binding or attachment of the reactant to a membrane surface, such as metal chelate adsorber membrane (for example, Sartobind's metal chelate absorbers). Metal chelate absorbers represent Immobilized Metal Affinity Chromatography (IMAC) purification devices. They can simply be used in an HPLC, FPLC or operated by hand with a syringe connected via Luer Lock. These IMAC devices can be attached to the reactant via a suitable Ex-tag, such a polyhistidine, because histidine containing proteins bind to immobilized metal ions. Especially strong interactions take place with the commonly used polyhistidine (His 6-tag) with six consecutive histidine residues. The MMV can now be incubated with a reactant which carries a polyhistidine as EX-tag and is therefore attached to the membrane and can be concentrated or isolated from cell lysates or culture supernatant, by incubating and filtrating.

In addition it has been shown that also enveloped viruses can be painted with such a reactant and thereby be tagged. The method of the invention now also provides for a method to simultaneously tag or tag and isolate viruses and MMV. This would allow a one-step purification of all such particles, a system independent of antibodies. This would allow much time and costs to be saved when diagnosing multiple diseases or detecting infectious agents and allow new agents to be potentially identified also. It does not abrogate the need to identify them after they have been purified but it does offer a great reduction in time and costs from the current best system as it potentially reduces the number of steps involved by 50% as well as greatly reducing the materials required for these upstream parts of the process which are by far greater than those required for the remaining latter parts.

Surprisingly, it is possible to detect MMV according to the methods of the invention without the need to isolate the vesicles (or viral particles) from the aqueous sample, such as a bodily fluid sample, a cell culture sample, or a cell culture medium sample, a physiological saline or a buffered saline sample, or any sample originating from such a bodily fluid sample, prior to incubating them with the reactant which is used to paint them.

One embodiment of the present invention therefore is a method for exogenously modifying the membrane composition of a MMV, comprising the steps of incubating an aqueous sample that comprises MMV with a reactant comprising a hydrophilic target domain or moiety covalently linked to an amphiphilic membrane anchor domain comprising of a lipophilic part and a hydrophilic part, wherein the lipophilic part of the membrane anchor domain becomes integrated into the lipid double layer of the membrane and wherein the hydrophilic part of the anchor domain, as well as the hydrophilic target domain become exposed to the surrounding aqueous sample fluid, and wherein the hydrophilic target domain or the hydrophilic part of the anchor domain carries an EX-tag. Such EX-tag may be a peptide a protein tag, which again may be attached to magnetic beads.

Preferably the EX-tag is a protein or peptide tag. A preferred protein or peptide tag in the embodiments described below would be a Histidine-tag (His-tag), FLAG-tag, Strep-tag, FLAG-tag, GST-tag, a Myc-tag, a HA-tag or an OMP A-tag or other single or several amino acid(s) that can be chemically modified to allow attachment of a second peptide or protein tag or bioactive molecule, or a chemical entity or an organic or non-organic micro- or nano- or bead or related type of particle, characterised as enabling the isolation of the so-tagged MMV (or enveloped virus particle).

A peptide tag herein is understood to comprise of at least one amino acid. The stretch of amino acids (sequence) of the peptide tag is characterised as enabling the binding to a biological, chemical or metal-based or metal-related reagent, designed for the purpose of binding to the tag and thereby allowing the isolation of the MMV.

This amino acid stretch may comprise a histidine (His-) tag, a Flag-tag, a strep-tag, a one Strep-tag, a GST-tag, a Myc-tag, a HA-tag or an OMP A tag, or other amino acid(s) which enable attachment of a second peptide or protein tag. It is a preferred embodiment wherein the EX-tag is an epitope tag. The epitope tag allows the according antibody to find the protein, or in this case the anchored protein, i.e. the membrane-modified vesicle, enabling lab techniques for localization, purification, and further molecular characterization. Common epitopes used for this purpose are c-myc, HA, FLAG-tag, GST and 6× or 10× His.

It is a more preferred embodiment wherein the EX-tag is a His tag, which is comprised of a consecutive run of not less than 6 and not more than 10 histidine residues.

In some embodiments the EX-tag may be chemically modified first, before it will be used for MP; for example the EX-tag may be consisting of a single cysteine, in which case only a reduction of the disulfide bond to a sulfhydryl group allows the attachment of a second molecule, such as an NHS ester of biotin, and subsequently then avidin or streptavidin for further purification or detection procedures.

In another embodiment of the invention these membrane modified MMV are first incubated with the reactant comprising a hydrophilic target domain or moiety covalently linked to an amphiphilic membrane anchor domain or moiety, wherein the lipophilic part of the membrane anchor domain becomes integrated into the lipid double layer of the membrane and wherein the hydrophilic target domain becomes exposed to the surrounding aqueous sample fluid, and wherein the hydrophilic target domain or the hydrophilic part of the anchor domain carries an EX-tag, such as preferably a peptide a protein tag, and then isolated, wherein isolated is meant to comprise the meanings of purified, concentrated or enriched for. The isolation may be from the sample fluid and/or excessive reactants. This isolating step is enabled by making use of the reactant that is now integrated into the MMV membrane and exposing the EX-tag (with or without magnetic beads) attached to it to the surrounding environment.

In another embodiment of the invention the sample comprises MMV and enveloped viral particles. In this embodiment both types of molecules (vesicles and viruses) are painted and therefore tagged as a result if an incubation step with the reactant comprising a hydrophilic target domain or moiety covalently linked to an amphiphilic membrane anchor domain or moiety, wherein the lipophilic part of the membrane anchor domain becomes integrated into the lipid double layer of the membrane and wherein the hydrophilic target domain becomes exposed to the surrounding aqueous sample fluid, and wherein the hydrophilic target domain or the hydrophilic part of the anchor domain carries a tag, preferably a peptide a protein tag. Concordantly both, the tagged MMV and the enveloped virus particles are isolated simultaneously.

In another embodiment the membrane modified vesicles, or the membrane modified vesicles and the membrane modified virus particles, are detected or visualized with the use of the reactant incorporated into the membrane. This is done after a prior step of purification or isolation of the painted vesicles or particles. It is especially preferred that these isolation methods comprise of a step which uses the EX-tag, such as for example a his affinity tag, that is attached to the hydrophilic target domain, or the hydrophilic part of the anchor domain, and hence after incorporation exposed to the outer surface of the MMV membranes or enveloped viral particle.

Obviously it is depending on the sample type and the detection method whether an enrichment step to concentrate the painted or successfully incubated MMV is necessary before detecting them. In case the sample comprising the MMV is of clinical nature the number of MMV will be very limited. Most clinical samples, i.e. body fluid samples, may only contain a small number of vesicles or viruses, such as below 100, below 50 or even below 10. In these cases a detection method that is able to detect tagged MMV or viruses in the background of the sample material (i.e. with no isolation or purification step) would require a very high sensitivity.

To our knowledge no such methods exist which do not require any form of concentration, purification, or enriching the vesicles and/or viral particles before detecting them. According to the invention the isolating step is facilitated by the EX-tag, which is linked to the hydrophilic target domain or the hydrophilic part of the anchor domain, which the sample comprising vesicles and or enveloped viral particles was incubated with. The attachment of the EX-tag enables an easy isolation step and furthermore the use of downstream detection/identification methods such as but not limited to polymerase chain reaction (PCR), reverse transcription PCR (rtPCR), real-time PCR (RT-PCR), ELISA, Dot blots, Western blots, Southern blots and/or various forms of electron microscopy (SEM, TEM).

It is therefore a preferred embodiment of the invention wherein the modification of the vesicles' membrane is followed by a step wherein the membrane modified MMV are isolated or purified by making use of the hydrophilic target protein or the attached tag before detection of said MMV.

It is preferred that the hydrophilic target domain carries the EX-tag, such as, for example, a protein tag, as defined above.

Because the incubation step works even without having to isolate the MMV first, it is one embodiment of the invention wherein the method for isolating, enriching or concentrating of MMV comprises of the step of incubating of an aqueous sample comprising MMV, that has not been enriched for said MMV prior to the incubation, with the reactant according to the invention (as described throughout the application), and wherein a sufficient MP reaction of the MMV, such as exosomes, is achieved.

It is further preferred that such a method is followed up by a step of isolating the membrane modified MMV from the sample by employing the introduced EX-tag.

It is a preferred embodiment wherein the first step of such a method is obtaining an aqueous sample that comprises MMV, which preferably are of a size of between 20 and 1000 nm, more preferably between 30 and 100 nm, and most preferably between 40 and 90 nm.

It is also a preferred embodiment of the method according to the invention wherein, a step of spinning down the sample with a suitable speed and time to separate cells and cell membrane debris from a supernatant containing MMV and does not cause the pelleting of vesicles or viruses, is added before the incubating step. It is preferred that the spinning speed is between 1.000-15.000 g and that the spinning time is between 0.5-30 min. A first spinning in a low speed centrifuge at for example 1000 g to 3000 g may be introduced to get rid of intact cells. This may be followed up by a second centrifugation step at higher speed, for example 8000-25000 g, to remove cell fragments.

By carefully collecting the supernatant in the next step a sample is obtained that is now free from cell membranes, thereby significantly reducing a possible background signal originating from "painted" cell membranes.

The supernatant is then incubated with the reactant according to the invention wherein said hydrophilic target domain carries a protein or peptide tag. During the incubating step MMV in the sample will incorporate the reactant into their membrane and expose the tag to the surrounding aqueous environment.

This feature can now be used to isolate or purify the MMV which carry the described protein or peptide tag and thereby to concentrate or enrich for them. In addition a step may be added to reduce excessive reactants, such as a centrifugation step to remove excessive tagged GFP-GPI for example.

The methods according to one embodiment of the invention allow for the protection, guiding and tracking of single vesicles or viruses, because, such modified particles or vesicles may be guided via magnets. This may also be useful for therapeutic purposes to deliver gene therapy vectors (e.g. MMV or viruses, loaded with therapeutic genetic information or proteins) or in research to study for example what the effects are when the particles are concentrated in certain tissues.

It is a preferred embodiment of all methods according to the invention that the MMV is an exosome, liposome or polymersome.

It is also preferred that the amphiphilic membrane anchor domain is selected from the group comprising phospholipid-polyethyleneglycol, stearyl, myristyl, cholesterol, chelator lipid nitrilotriacetic acid ditetradecylamine (NTA-DTDA) and glycosylphosphatidylinositol (GPI) or man made mimics thereof. Man-made mimics of GPI and the like are understood to be synthetically generated or altered variants of these molecules, which do not occur in nature natively, but mimic the properties of the native molecules.

It is also preferred that the hydrophilic target domain is selected from the group containing proteins, polypeptides, polysaccharides, nucleic acids, dyes, radioactive ligands, fluorescent dyes, protein and peptide tags carrying synthetic beads or magnetic particles, wherein the synthetic beads or the magnetic particles can be coated or uncoated. It is particularly preferred that the hydrophilic target domain is a protein or a polypeptide, though. It is even more preferred that such protein or polypeptide carries the EX-tag (such as a peptide tag or protein tag) or several of these or even combinations of such.

In a preferred embodiment of all methods the reactant is a GPI-anchored protein, either a naturally occurring GPI-anchored protein or a synthetic copy or chemical mimic thereof.

Further the invention comprises MMV of a diameter between 30 and 100 nm, characterised by carrying in its phospholipid bilayer membrane a recombinant and/or tagged reactant comprising a hydrophilic target domain covalently linked to an amphiphilic membrane anchor domain or moiety, wherein the lipophilic part of the membrane anchor domain becomes integrated into the lipid double layer of the membrane and wherein the hydrophilic target domain becomes exposed to the surrounding aqueous sample fluid, wherein it is preferred that it carries an EX-tag, preferably a peptide or protein tag, enabling its isolation or extraction from a background solution.

In a preferred embodiment the size of the MMV is between 40 and 90 nm of diameter. It is also preferred that the hydrophilic target domain or moiety is selected from the group comprising proteins, polypeptides, polysaccharides, nucleic acids, dyes, radioactive ligands, fluorescent dyes, and protein and peptide tags carrying synthetic beads or magnetic particles, wherein the synthetic beads or the magnetic particles can be coated or uncoated.

It is also preferred that the amphiphilic membrane anchor domain is selected from the group comprising phospholipid-polyethyleneglycol, stearyl, myristyl, cholesterol, chelator lipid nitrilotriacetic acid ditetradecylamine (NTA-DTDA) and glycosylphosphatidylinositol (GPI) or man made mimics thereof. Man made mimics thereof comprise for example analogues of GPI-anchor domains wherein portions of the glycan core are systematically replaced with unnatural linkers of comparable length and dimension. Those analogues might contain nil, one or two mannose units and replace the phosphoinositol and glucosamine units with a simple hydrophilic poly(ethylene glycol) linker which allows for the installation of various side chains and different lipid tails.

In the most preferred embodiment the MMV is characterised by carrying a recombinant and/or tagged GPI-anchored protein in its membrane. It is preferred that the hydrophilic target domain of the reactant, or the hydrophilic protein part of the GPI-anchor, carries an EX-tag, such as a molecular or biochemical label, preferably a protein or peptide tag, as described above.

It is preferred that this tag is selected out of the same group of compounds as is described for the method embodiments of the invention, above.

It is a preferred embodiment of the invention, wherein the hydrophilic target domain and the amphiphilic membrane anchor domain are chemically joined by a cross linker.

In a preferred embodiment of the invention, the incubation step is achieved by slow agitation. It is preferred that the "molecular painting" of the vesicles or viruses is performed in body fluid, cell culture medium, buffered saline or physiological saline; preferably at temperatures between 4 to 60° C., more preferably between 15 and 45° C., and most preferably at temperatures between 30 and 37° C.; for incubation times between 10 seconds and 48 hours, preferably between 5 min and 3 hours, more preferably between 10 min and 2 hours and most preferably between 20 and 40 mins.

In a preferred embodiment the samples are incubated at 37° C. for 30 minutes under a 360 degree 'rotate and shake' motion.

A further aspect of this invention therefore is a method for aiding in the identification of new MMV potentially associated with a disease or other medical condition, comprising the steps of obtaining a biological sample from a subject; isolating a MMV fraction from the sample; and detecting within the MMV fraction species that do not express any of the characteristic MMV marker proteins, preferably the MMV is an exosome.

Furthermore the invention pertains to uses of membrane modified MMV according to the invention and uses of methods according to the invention for the discovery of new MMV. New MMV, are understood to be MMV, which expose at their surface antigens and proteins that were not so far associated with MMV, or which lack one or more of the so called marker proteins. It is preferred that these MMV are exosomes.

The fact that the MMV can be painted, or marked with a reactant that is incorporated into their membrane, independently from any antigens being presented at the surface of the vesicles opens new possibilities to isolate batches of MMV comprising so far unknown types of MMV, which may not present the thought-to-be characteristic antigens on their surface.

Therefore one method according to the invention that is for isolating, enriching or concentrating of MMV comprises the steps of (a) incubating an aqueous sample comprising MMV with a reactant comprising a hydrophilic target domain or moiety covalently linked to an amphiphilic membrane anchor domain or moiety, wherein the lipophilic part of the membrane anchor domain becomes integrated into the lipid double layer of the membrane and wherein the hydrophilic target domain becomes exposed to the surrounding aqueous sample fluid, and (b) isolating, enriching or concentrating of membrane modified/molecular painted (MP) MMV from the sample fluid and/or excessive reactants and is followed by a step of identifying MMV, that are characterised as showing unexpected properties, that have not been described for MMV before.

MMV, especially exosomes, are believed to carry along important information in form of cancer cell derived proteins as biomarkers etc., so they are collected from bodily fluids. To isolate cancer-derived exosomes size exclusion chromatography is used or a size exclusion chromatography fraction followed by centrifuging a chromatography fraction comprising the cancer-derived exosomes. Cancer-derived exosomes may be separated from non-cancer-derived exosomes by immunosorbent capture using an anticancer antigen antibody.

Another method to prepare an immunogenic MMV comprises isolating or purifying a MMV from a biological sample and contacting the MMV with a peptide or a lipid under conditions allowing the peptide or lipid to bind an antigen-presenting molecule at the surface of the MMV.

The methods according to the invention, such as for example GPI-tagging, allow for specific concentration of known or unknown MMV in any given sample, preferably in bodily fluid, cell culture medium or buffered saline.

Therefore, new applications for MMV purification and/or concentration and/or isolation are presented. This tool may conceivably develop as a major component of a new diagnostics system to quickly and easily purify and identify and/or quantify known or unknown MMV from biological samples, research samples or clinical samples.

According to the methods of the invention the biomarkers contained in or carried along by the MMV can now be captivated and used for diagnosis by isolating the MMV by using one of the methods described above. The invention furthermore comprises uses of the membrane modified MMV for diagnostic purposes, or for diagnosing a disease based on the properties of the isolated MMV or the biomarkers contained therein, especially the use of membrane modified exosomes, characterised as having incorporated into its membrane a reactant comprising of an amphiphilic membrane domain and a protein, such as a GPI-anchored protein, carrying a peptide tag, such as a his tag, to make the MMV accessible to capturing methods which make use of the tag. It is preferred that this is done via magnetic beads or particles, as is described in the examples.

A preferred method for diagnosing a disease based on biomarkers found in MMV, would comprise steps as obtaining a sample from a patient comprising MMV; spinning down the sample at a suitable speed to remove cell debris and cell membrane fragments, for example at 10K-40K g for 0.5-30 min; incubating the supernatant comprising MMV with a GPI-anchored protein, wherein the protein carries an EX-tag, for example a peptide tag; isolating the membrane modified/MP MMV from the supernatant; analysing the MMV with regard to the presence of biomarkers for use in diagnosing a disease based on biomarkers found in MMV.

MMV MP allows for the direct labeling of MMV membranes, thus facilitating concentration, purification and/or visualization of MMV e.g. for diagnostic purposes. Incorporation of specific chemical moieties into membranes of MMV are also useful for lowering of detection limits in common qualitative and quantitative immunoassays, such as ELISA or for PCR and/or FACS analysis. The methods presented herein are especially useful as part of a diagnostic system or diagnostic kit. Furthermore they can be used for isolation, detection, or measurement of known or unknown MMV, preferably exosomes.

In another embodiment the MMV may be incubated with a reactant according to the invention and hence be membrane-modified ex vivo and then replaced in vivo, where they can be tracked and imaged allowing for the basic understanding of the roles these MMV play in the animal or human body or for monitoring disease progression.

In one embodiment prior to the incubation step is that the cell membrane and cell debris are removed from the sample, then the sample comprising MMV or MMV and potentially also enveloped viral particles is incubated with a reactant according to the invention and hence the MMV or the MMV plus enveloped viruses therein are membrane modified. Finally the painted MMV or the MMV plus enveloped viruses therein are placed into a different setting, such as into a living a cell or organism, for example, a body or a plant. It would now be possible to study the fate of the painted MMV or MMV plus viral particles in that new setting. It is preferred that the new setting is an in vivo situation. It is now possible to track the MMV and/or viral particles using magnetic resonance imaging (MRI) if the tag (EX-tag) painted to the outer surface of the MMV and/or viral particles' membranes is attached to a magnetic nanoparticle for example. In another preferred embodiment the membrane anchor domain is GPI and the hydrophilic target domain is GFP, hence the MMV are GFP-GPI painted. This enables the use of in vivo imaging systems (e.g. IVIS) to track the movement and localization of the painted MMV, preferably exosomes, or of the MMV and viral particles simultaneously.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

EXAMPLES

Example 1—Obtaining Samples Comprising Exosomes

8×T175 flasks of HEK293T cells were cultured in DMEM until 80-90% confluency. The adherent cells are washed once in 10 ml of PBS, and 18 ml of serum-free DMEM is added into each flask. The cells are incubated in $CO_2$ incubator at 37° C. for approximately 24 hours. After 24 hr incubation, the supernatants (containing exosomes secreted from the cells) are collected.

By combining the supernatants of two flasks 4×36 ml of cell supernatant were placed in 4×50 ml falcon tubes and centrifuged at 1200 g for 8 minutes at 4° C. 4×35 ml of the supernatant are carefully pipetted up, leaving 1 ml of supernatant and the cell debris in the falcon tube.

The supernatant sample is now centrifuged again at 8400 rpm (approx. 12,000 g) for 15 minutes at 4° C. to remove smaller fragments of the cells and cell membranes. After centrifuging, 4×34 ml of the supernatant is taken out and placed into 4× new tubes. 1 ml of supernatant and any remaining cell debris is left in the used tube.

Example 2—Standard Purification of Exosomes Via Ultracentrifugation

After the intermediate centrifugation step, 4×34 ml of the supernatant were taken out and placed into 4× new ultracentrifuge tubes. 1 ml of supernatant and any remaining cell debris was left in the used tube. The supernatant samples (within the 4 new ultracentrifuge tubes) are centrifuged at 26,500 rpm (~120,000 g) for 2 hours at 4° C. After centrifugation, the supernatant is discarded and the tube is carefully blotted dry. The remaining pellets (containing exosomes) are resuspended in 2.5 ml of PBS by washing the bottom of the tube. From this 2.5 ml resuspended exosome sample is 5×500 ul samples have been transferred into 5 tubes and labelled as follows:

1) E−: unpainted exosomes, ultracentrifuged (control)
2) E+: painted exosomes, ultracentrifuged (to get rid of unbound gfp-gpi protein)
3) E−MB+: unpainted exosomes, applied over pre-coated beads and subsequently eluted
4) E−MB−: unpainted exosomes applied over non-coated beads and subsequently eluted 5) E+MB−: painted exosomes (including unbound gfp-gpi) applied over non-coated beads and subsequently eluted Each of the five samples used in the following experiments comprises the same amount of exosomes.

Example 3: Generation of His-Tagged GPI-GFP Protein

The HEK 293 cell line used has been altered to produce the his-tagged and monomeric version of the GPI-GFP protein that is used in the example and to be resistant against hygromycin. In the lab the cells are referred to as "HEK293monogghishyg cells". They were grown up in a medium which contains 500 ml DMEM high-glucose (Invitrogen 11960 or 11965), 50 ml deactivated FBS (PAAA15-101), 5 ml of 100 mM Sodium Pyruvate (Gibco 11360) and 5 ml of 200 mM L-glutamine (Gibco 25030).

Finally, hygromycin was added to a final concentration of 50 ug/ml. The cells were grown up in 5-6 T175 flasks to near confluency, then the cell medium was discarded and the cells were washed with 5 ml PBS per flask and then scraped off. The scraped cells from the flasks were collected in 10 ml of PBS each and all flasks rinsed out carefully. The PBS cell suspension was then centrifuged in 15 ml Falcon tubes and centrifuged at 200 g, for 5 mins, at 4° C.

The supernatant was discarded and 25 ml of sample application buffer was added to the pellets. The sample application buffer (50 mM Tris, 50 mM NaCl, 35 mM Imidazole, 1% w/v OG, pH 7.4) contains 1% w/v n-Octyl-ß-D-glucopyranoside (OG) which solubilises the GPI proteins from the cell membrane. After addition of 100 ul of protease inhibitor cocktail (Sigma) the samples are incubated at 4° C. for 30-60 min.

The solubilised protein sample was centrifuged at 2000 g 30 mins, 4° C. and then collected to be purified with an FPLC. The column used was a his-trap (Ni-IMAC) column. The supernatant of the centrifuged sample was filled into 50 ml syringe with avoidance of bubbles and then applied to the port. In order to identify the fractions which comprise the GPI-protein Western Blots were performed on the loading and elution fractions, those which comprise the protein are pooled.

Finally the eluted GPI-mono-his tag protein in this pool was concentrated by ultrafiltration with 10MCWO membranes. Protein containing fractions from the eluate were pooled and ultracentrifuged through the ultrafiltration device at around 3500 g until all the fractions were added and dead stop volume was reached. The collected proteins on the filter were then washed with two times 10 ml of a buffer comprising 50 mM Tris and 50 mM NaCl centrifuged through the filter device.

Example 4: Molecular Painting of Exosomes with HIS-Tagged GPI-GFP Protein

The samples from example 2 labelled 2 and 5 were painted: 17.5 ug of purified his-tagged GPI-GFP protein (in a buffer consisting of 50 mM Tris and 50 mM NaCl) were added to samples 2 and 5. An equivalent amount of the same buffer solution was added to samples 1, 3 and 4.

The samples ('2' and '5') were incubated at 37° C. for 30 minutes under a 360 degree 'rotate and shake' motion, at setting "F6" using the "intellimixer" rotation device from Neo-Lab, at 20 rpm. The "F6" motion program is best described as a vertical rotary motion about the central axis of the Eppendorf tube (so the Eppendorf goes head-over-heels). Every 120 degrees or ⅓ of a circle, it pauses and does a vibration to dislodge liquid droplets that might be clinging on to the bottom of the tube (or the top).

Example 5: Molecular Painting of Magnetic Beads with HIS Tagged GPI-GFP Protein 4×30 ul of Promega magnetic beads were aliquoted out and washed once in MB wash/bind buffer (100 mM HEPES, 10 mM Imidazole, 500 mM NaCl, pH 7.5). 17.5 ug of purified his-tagged GFP-GPI was added into one MB sample (meant for exosome sample 3) and incubated for 5 minutes, before washing with 3×500 ul of MB wash/bind buffer.

Example 6

This was a proof-of-concept experiment to show that a) exosomes do stick to membrane anchor domain proteins, such as GPI-like proteins, that are tagged with a HIS-tag, and that this tag could be used to isolate the painted exosomes from a sample via magnetic beads and b) exosomes do stick to magnetic beads if these have been pre-coated with the GPI-like protein that carries a HIS-tag to stick to the magnetic beads at one end and carries a lipophilic part to stick to membranes on the other hand. For this experiment five samples have been used which contain the same amount of exosomes (see Example 2).

Sample 3 comprising the unpainted exosomes as achieved in Example 2 (sample labelled 3) was incubated at 37° C. for 30 minutes under a 360 degree 'rotate and shake' motion, (at setting "F6" using the "intellimixer" rotation device from Neo-Lab, at 20 rpm) before it was added to the pre-coated magnetic beads. The flow-through was discarded.

After samples 1 and 2 (sample 2, comprising painted exosomes, sample 1 (control), comprising exosomes only) were incubated at 37° C. for 30 minutes under a 360 degree 'rotate and shake' motion, (at setting "F6" using the "intellimixer" rotation device from Neo-Lab, at 20 rpm), they were transferred in clean ultracentrifuge tubes with 35 ml of PBS. These are then ultracentrifuged at 21,000 rpm for 2 hrs 4° C. At this speed exosomes are being pelleted but unbound GFP remains in solution. The supernatant was discarded and the tube was carefully blotted dry. The remaining pellet comprising the exosomes was carefully washed with 500 ul of buffer.

Samples 4 (unpainted exosomes) and 5 (painted exosomes) were added to uncoated magnetic beads. Samples 4 and 5 were applied onto one aliquot of uncoated magnetic beads each, incubated for 10 minutes, and the flow-through discarded. The magnetic beads were then washed 3×500 ul with wash/bind buffer. 100 ul of elution buffer (100 mM HEPES, 500 mM Imidazole, pH 7.5) was added to the beads and incubated for 10 minutes at room temperature. The 100 ul eluates were collected. 20 ul of 5× sample buffer (for western blot) were added.

20 ul of sample buffer (for western blot) was added to samples 1 and 2.

Finally, each sample was in a volume of 120 ul in sample buffer, ready for the western blot.

Example 7: Western Blot

The samples were divided into two samples a 50 ul, and used for two different gels:

50 ul of the samples were loaded into 2× Invitrogen Nupage bis-tris 4%-12% gels with appropriate markers and controls. Gels were run using a Hoefer Gel electrophoresis set at 90-120 v for approximately 2.5 hours. After electrophoresis, gels were transferred into PVDF membrane using a semi-dry blotter at 90 mA for 1 hr 15 mins. The 2 membranes were incubated in blocking buffer:

One membrane, which was later incubated with the anti-GFP antibody, was incubated overnight in 50 ml of 4% skim milk, 1% BSA under a gentle rocking motion. The following day the membrane was incubated in 5 ml of TTBS solution (150 mM NaCl, 20 mM Tris pH8, 0.2% v/v Tween 20) with 5 ul of rabbit anti-gfp antibody for 2 hrs.

The second membrane (referred to as anti-PDC6I membrane) was first incubated for 1 hr in 50 ml of 10% skim milk and then incubated in 5 ml of blocking solution which contained 2.5 ul of mouse anti-PDC6I antibody (1:2000) overnight, under horizontal rotation inside a 50 ml falcon tube. PDC6I is a known exosome biomarker.

Both membranes were then washed 5×50 ml TTBS.

The anti-GFP membrane was then incubated with 1 ul of mouse anti-rabbit HRP secondary antibody in 5 ml of TTBS (1:5000) for 2 hrs. The anti-PDC6I membrane was then incubated with 1 ul of swine anti mouse-HRP secondary antibody in 5 ml of TTBS (1:5000) for 2 hrs.

Both membranes were then washed 5×50 ml×5 mins in TTBS and 1×50 ml×5 mins in TBS (150 mM NaCl, 20 mM Tris pH8).

3 ul of ECL plus chemiluminescent reagent was used to visualise the western blot using an Alpha-Innotech gel doc system.

Figure 2:
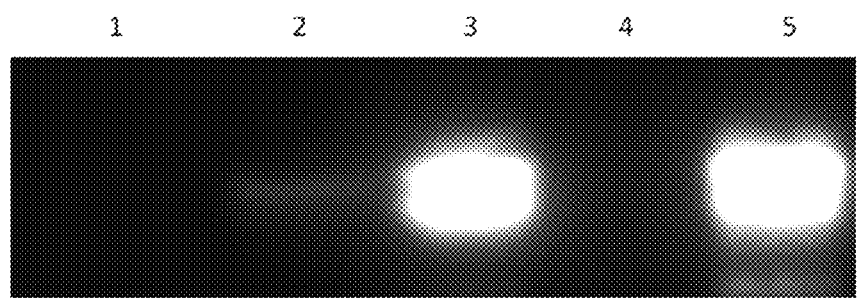
FIG. 2 shows a photograph taken from the Western-Blot of the membrane that was incubated with the GFP specific antibody anti-GFP. The numbers are indicating the lanes that were used and they correspond to the samples prepared (sample 1 in lane 1 etc.).

Results:

The result in lane 1 of FIG. 1 shows sample 1 has reacted with the anti-PDC6I antibody, indicating that exosomes are present in the exosome sample, still after the ultracentrifugation step (introduced to remove excess GFP-GPI). Hence all the samples, prepared in example 1, which have been used for Molecular Painting contain exosomes. FIG. 2 confirms that exosomes do not usually react with anti GFP antibodies.

The result in lane 2 (sample 2) shows that exosomes are still present (FIG. 1) and GFP is still associated with them (FIG. 2), even after the ultracentrifugation step. The ultracentrifugation step would have got rid of excessive GFP hence the MP was successful.

The result in lane 3 (sample 3) shows that the eluate from the magnetic beads contains exosomes (FIG. 1), indicating that the exosomes were associated to the pre-coated beads and could be eluted therefrom, and were not discarded with the flow-through. From the signal in lane 3 of FIG. 2 it can be seen that the exosomes in the eluate carried GFP-anchor proteins and that indicates that the unpainted exosomes attached themselves to the reactant, a tagged GFP-GPI-anchor protein which was attached to the magnetic beads via the HIS-tag, while being incubated with said reactant on the beads.

The fact that the signal in lane 2 of the anti GFP blot (FIG. 2) is much less intense than the signal in lane 3 (and 5) may be explained by the ultracentrifugation step which might have removed not only the excessive GFP-proteins but might also have potentially reduced the amount of exosomes in the supernatant.

The result in lane 4 (FIG. 1) shows that only some minor background signal is detectable with the exosome antibody, when unpainted exosomes are applied to non-coated beads, and the flow-through is discarded. As expected there is no signal on the anti-GFP blot.

The result in lane 5 shows that exosomes are present in the eluate of sample 5 after the exosomes have been painted and applied to magnetic beads, and the flow-through was discarded. The MP worked, as can be seen from FIG. 2 representing the anti-GFP blot. The exosomes were associated with the magnetic beads via the HIS tag, which was part of the reactant the exosomes were painted with.

The invention claimed is:

1. A method for exogenously modifying the membrane composition of a membrane microvesicle (MMV), comprising
    incubating an aqueous sample comprising MMV with a reactant comprising a hydrophilic target domain or moiety covalently linked to a lipophilic membrane anchor domain or moiety, wherein the lipophilic membrane anchor domain becomes integrated into the lipid double layer of the membrane and wherein the hydrophilic target domain becomes exposed to the aqueous sample fluid,
    wherein the hydrophilic target domain of the reactant carries one or more extraction (EX)-tags.

2. A method for isolating, enriching or concentrating of MMV, comprising the steps
    (a) incubating an aqueous sample comprising MMV with a reactant comprising a hydrophilic target domain or moiety covalently linked to a lipophilic membrane anchor domain or moiety, wherein the lipophilic membrane anchor domain becomes integrated into the lipid double layer of the membrane thereby providing membrane modified MMV, wherein the hydrophilic target domain becomes exposed to the surrounding aqueous sample fluid, and wherein the hydrophilic target domain of the reactant carries an EX-tag, and
    (b) isolating membrane modified MMV from the sample fluid and/or excessive reactants, with the use of said tag.

3. A method according to claim 2, wherein the aqueous sample comprises MMV and enveloped viral particles, wherein the lipophilic membrane anchor domain becomes integrated into the envelope of the enveloped viral particles thereby providing membrane modified viral particles, and wherein after the incubating step, membrane modified vesicles and membrane modified viral particles are isolated simultaneously.

4. A method according to claim 3, wherein the steps are followed by an additional step of detecting the membrane modified MMV, or detecting the membrane modified viral particles simultaneously with the membrane modified MMV.

5. A method according to claim 1, wherein the lipophilic membrane anchor domain is selected from the group consisting of phospholipid-polyethyleneglycol, stearyl, myristyl, cholesterol, chelator lipid nitrilotriacetic acid ditetradecylamine (NTA-DTDA) and glycosylphosphatidylinositol (GPI) or man made mimics or analogues thereof.

6. A method according to claim 1, wherein the hydrophilic target domain is selected from the group consisting of proteins, polypeptides, polysaccharides, nucleic acids, dyes, radioactive ligands, fluorescent dyes, or protein or peptide tags, which preferably carry synthetic beads or magnetic particles, wherein the synthetic beads or the magnetic particles can be coated or uncoated.

7. A method according to claim 1, wherein the hydrophilic target domain is a protein or a polypeptide.

8. A method according to claim 1, comprising the additional steps of preparing a sample for incubation by
    removing cell membranes;
    spinning down the aqueous sample to remove cells, cell debris, such as membrane fragments; and collecting the supernatant and providing this as sample to be incubated.

9. A method according to claim 1, wherein the aqueous sample is a bodily fluid or originating therefrom, a cell culture medium sample, a physiological saline or a buffered saline sample.

10. A method according to claim 1, wherein the MMV is an exosome.

11. A method according to claim 1, wherein the reactant is a GPI-anchored protein.

12. A method according to claim 1, wherein the EX-tag is a protein or peptide tag selected out of the group of Histidine-tag, FLAG-tag, Strep-tag, GST-tag, Myc tag, HA tag, OMPA tag and other single or several amino acid(s) that can be chemically modified to allow attachment of a second peptide or protein tag or bioactive molecule, or a chemical entity or an organic or non-organic micro- or nano- or bead or related type of particle.

13. A method according to claim 12, wherein the EX-tag is a single cysteine residue wherein reduction of its disulfide bond to a sulfhydryl group allows the attachment of a second molecule and subsequently then avidin or streptavidin for further purification, isolation or detection.

14. A method according to claim 1, wherein the EX-tag is characterised as carrying magnetic beads or particles.

15. The method of claim 1, wherein the MMV comprises genetic material.

\* \* \* \* \*